(12) United States Patent
Millikan

(10) Patent No.: US 10,568,517 B2
(45) Date of Patent: Feb. 25, 2020

(54) VIEWING AND PROCESSING MULTISPECTRAL IMAGES

(71) Applicant: Thomas Nathan Millikan, San Diego, CA (US)

(72) Inventor: Thomas Nathan Millikan, San Diego, CA (US)

(73) Assignee: Thomas Nathan Millikan, San Diego, CA (US)

( * ) Notice: Subject to any disclaimer, the term of this patent is extended or adjusted under 35 U.S.C. 154(b) by 0 days.

(21) Appl. No.: 16/429,011

(22) Filed: Jun. 2, 2019

(65) Prior Publication Data

US 2019/0282100 A1    Sep. 19, 2019

Related U.S. Application Data

(63) Continuation of application No. 15/996,526, filed on Jun. 4, 2018, now Pat. No. 10,413,189, which is a
(Continued)

(51) Int. Cl.
*A61B 5/00* (2006.01)
*G06T 7/90* (2017.01)
*G01J 3/28* (2006.01)
*G01J 1/58* (2006.01)
*G01J 3/22* (2006.01)
(Continued)

(52) U.S. Cl.
CPC .......... *A61B 5/0075* (2013.01); *A61B 5/0077* (2013.01); *A61B 5/743* (2013.01); *G01J 1/58* (2013.01); *G01J 3/027* (2013.01); *G01J 3/0208* (2013.01); *G01J 3/0229* (2013.01); *G01J 3/0264* (2013.01); *G01J 3/10* (2013.01); *G01J 3/14* (2013.01); *G01J 3/2823* (2013.01); *G01J 3/36* (2013.01); *G01J 3/513* (2013.01); *G06T 7/0012* (2013.01); *G06T 7/90* (2017.01); *H04N 5/23293* (2013.01); *H04N 5/332* (2013.01); *H04N 7/18* (2013.01); *H04N 7/183* (2013.01); *H05K 999/99* (2013.01); *A61B 5/0071* (2013.01); *A61B 5/1112* (2013.01); *A61B 2560/0242* (2013.01); *A61B 2576/00* (2013.01); *G01J 2003/1213* (2013.01); *G01J 2003/2826* (2013.01); *G06T 2207/10024* (2013.01);
(Continued)

(58) Field of Classification Search
CPC ..... A61B 5/0075; A61B 5/0077; A61B 5/743; G06T 7/90; G06T 7/0012; G01J 1/58; G01J 3/0208; G01J 3/0229; G01J 3/0264; G01J 3/027; G01J 3/10; G01J 3/14; G01J 3/2823; G01J 3/36; G01J 3/513; H04N 5/332; H04N 5/23293; H04N 7/18; H04N 7/183; H05K 999/99
USPC ......................................................... 348/77
See application file for complete search history.

(56) References Cited

U.S. PATENT DOCUMENTS 5,784,162 A *  7/1998  Cabib ................. C12Q 1/6841
                                                    250/461.2
8,026,942 B2 * 9/2011  Payonk ............... A61B 5/0071
                                                    348/77
(Continued)

*Primary Examiner* — Patricia I Young

(57) ABSTRACT

Multispectral images, including ultraviolet light and its interactions with ultraviolet light-interactive compounds, can be captured, processed, and represented to a user. Ultraviolet-light related information can be conveniently provided to a user to allow the user to have awareness of UV characteristics and the user's risk to UV exposure.

19 Claims, 12 Drawing Sheets

Related U.S. Application Data continuation of application No. 14/866,973, filed on Sep. 27, 2015, now Pat. No. 9,986,912, which is a continuation of application No. 13/784,824, filed on Mar. 5, 2013, now Pat. No. 9,173,570.

(60) Provisional application No. 61/623,068, filed on Apr. 12, 2012.

(51) Int. Cl.

| | | |
|---|---|---|
| G01J 3/26 | (2006.01) | |
| G01J 3/14 | (2006.01) | |
| G01J 3/36 | (2006.01) | |
| G01J 3/51 | (2006.01) | |
| G06T 7/00 | (2017.01) | |
| H04N 5/33 | (2006.01) | |
| H04N 7/18 | (2006.01) | |
| H04N 5/232 | (2006.01) | |
| G01J 3/02 | (2006.01) | |
| G01J 3/10 | (2006.01) | |
| A61B 5/11 | (2006.01) | |
| G01J 3/12 | (2006.01) | |

(52) U.S. Cl.
CPC .............. *G06T 2207/10048* (2013.01); *G06T 2207/30088* (2013.01); *G06T 2207/30196* (2013.01)

(56) References Cited

U.S. PATENT DOCUMENTS

| | | | |
|---|---|---|---|
| 8,849,380 B2* | 9/2014 | Patwardhan | A61B 5/0059 600/476 |
| 2012/0022472 A1* | 1/2012 | Miura | A61B 5/0059 604/290 |

* cited by examiner

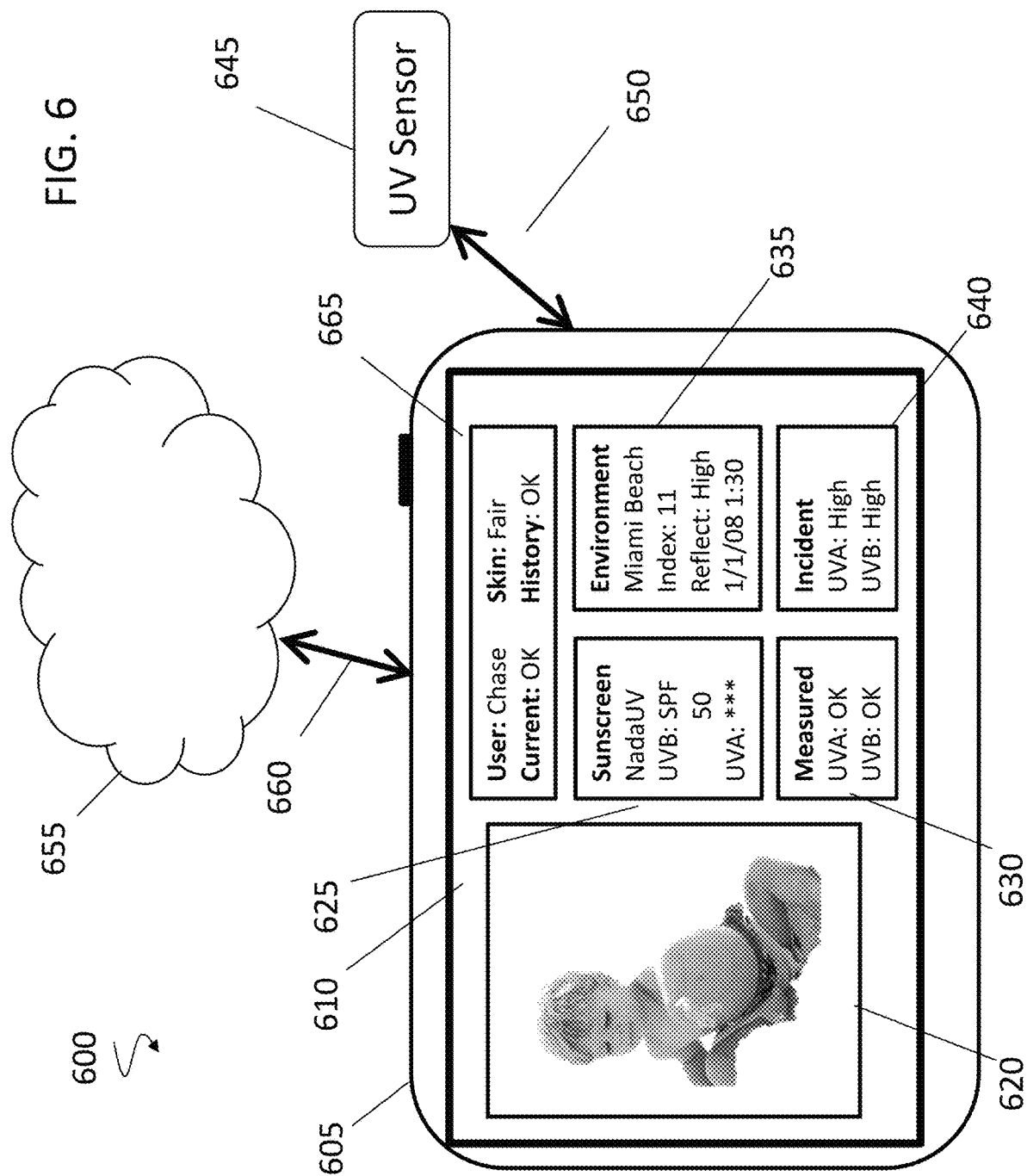

VIEWING AND PROCESSING MULTISPECTRAL IMAGES

CROSS-REFERENCE TO RELATED APPLICATIONS

This application is a Continuation of U.S. patent application Ser. No. 15/996,526 filed on Jun. 4, 2018, which is a continuation of U.S. patent application Ser. No. 14/866,973 filed on Sep. 27, 2015, now U.S. Pat. No. 9,986,912, which is a continuation of U.S. patent application Ser. No. 13/784,824 filed on Mar. 5, 2013, now U.S. Pat. No. 9,173,570, which claims priority to U.S. Provisional Application 61/623,068 filed on Apr. 12, 2012 entitled "Viewing and Processing Multispectral Images," which are incorporated herein in their entirety.

TECHNICAL FIELD

The present disclosure relates to multispectral images, and to materials, compounds, methods, and systems for viewing and processing multispectral images.

BACKGROUND

The sun produces radiation in a variety of wavelengths, many of which are not visible to the human eye. FIG. 1 shows a solar radiation spectrum 100. Sun 105 outputs radiation (or light) in a variety of wavelengths, including infrared light 130, visible light 125, ultraviolet A light 120, ultraviolet B light 115, and Ultraviolet C light 110. Ultraviolet A (UVA) light has wavelengths between 315 to 400 nanometers. Ultraviolet B (UVB) light has wavelengths between 280 to 315 nanometers. Ultraviolet C (UVC) light has wavelengths between 100 to 280 nanometers. UVA, UVB, and UVC light are invisible to the human eye. Visible light has wavelengths between 400 to 780 nanometers. Infrared has wavelengths between 780 nanometers and 1 millimeter and is invisible to the human eye.

FIG. 2 shows the transmission and absorption of component spectra in radiation spectrum 100 as the radiation travels from the Sun through the Earth's atmosphere and encounters human skin. Human skin 240 is composed of two layers—the epidermis 220 (i.e. outer lay) and the dermis 235. UVA and UVB light interact with human skin in different ways and cause different maladies. Both UVA and UVB light can harm a person's skin. UVA light, which can penetrate human skin more deeply than UVB light, is known to play a role in skin aging, wrinkling, and skin cancer. UVB light is the chief cause of skin reddening and sunburn, and also plays a key role in the development of skin cancer. Among other factors, the skin's response to UVA light and UVB light depends to some degree upon skin type, e.g., whether a person's skin is lighter or darker. Darker skin has more melanin, which offers a higher degree of protection from UV light.

Referring to FIG. 2, UVC light 110 can be transmitted 205 and absorbed by the Earth's atmosphere 210. Some UVB light 115 also can be transmitted 215 and absorbed by the Earth's atmosphere 210, but a portion is transmitted 215. UVA light 120 generally is not absorbed by the Earth's atmosphere 210 and is transmitted 230. UVB 215 can be absorbed by epidermis 220. UVA 120 can penetrate the epidermis 220 into the dermis 235.

Sunscreens (e.g. sunblock) are topically-applied lotions made to protect a person's skin from exposure to UVA light and/or UVB light. Sunscreens may include chemical or physical filters. Chemical filters form a thin, protective film on the skin's surface to absorb the UV radiation before it penetrates the skin. Physical filters are particles that are disposed on the skin's surface and reflect UV light.

Even broad-spectrum sunscreens that protect against UVA light and UVB light provide only limited protection. FIG. 3 illustrates coverage problems associated with improper sunscreen application. Picture 300 shows a boy 315 playing at the beach. The boy 315's current UV coverage is inconsistent. For example, spots 310, 320, 325, and 330 correspond to locations in which the sunscreen coverage is less effective. Such spots can result from a variety of factors, including improper application, dissipation from activity or swimming, and uneven wear. As a result of coverage problems, undetectable imbalances in protection frequently arise.

SUMMARY

The present inventor recognized the need to effectively determine the coverage on a surface, such as skin, of materials and compounds that interact with non-visible light, including sunscreen. Further, the inventor recognized the need to assess the UV exposure relative to a particular set of UV characteristics, including UV intensity, UV sensitivity, and coverage of UV-interactive materials and compounds.

In general, in one aspect, the techniques can be implemented to include capturing, in an image capture device, a UV light image; capturing, in the image capture device, a corresponding visible light image; processing the corresponding visible light image to identify an area of interest in the visible light image; and identifying a portion of the area of interest by comparing UV light image intensity in the area of interest to a UV light threshold. Further, the techniques can be implemented such that the area of interest is a portion of skin. Further, the techniques can be implemented such that the UV light threshold is based on the UV characteristics of a topical compound. Further, the techniques can be implemented such that the topical compound is sunscreen. Further, the techniques can be implemented to include rendering a display image from the UV light image and corresponding visible light image; and displaying the display image. Further, the techniques can be implemented such that the rendering includes using a color to represent the identified portion. Further, the techniques can be implemented such that the UV light image is a UVB light image. Further, the techniques can be implemented such that the UV light threshold is determined by comparing one area of the UV light image to another area of the UV light image.

In general, in another aspect, the techniques can be implemented to include a camera sensor operable to capture one or more UV light images; and a processor configured to identify one or more areas of interest by comparing the UV light image intensity with a UV light threshold; wherein the processor is further configure to render a display image that indicates the one or more areas of interest. Further, the techniques can be implemented such that the UV light threshold is based on the UV characteristics of a topical compound. Further, the techniques can be implemented such that the topical compound is sunscreen. Further, the techniques can be implemented to include means to obtain information comprising a type of sunscreen; means to obtain the UV characteristics for that type of sunscreen; and wherein the processor is further operable to use the UV characteristics to set the UV light threshold. Further, the techniques can be implemented such that the one or more UV light images comprise a UVA light image and a corresponding UVB light image; and wherein the one or more areas of interest comprise an area of interest in a UVA image and an area of interest in a UVB image. Further, the techniques can be implemented such that the display image has been rendered to use one color to represent the UVA area of interest and another color to represent the UVB area of interest. Further, the techniques can be implemented such that the camera sensor is operable to capture one or more corresponding visible light images; and the display image comprises visible light image information. Further, the techniques can be implemented such that the camera sensor is further operable to capture an infrared image.

In general, in another aspect, the techniques can be implemented to include a camera sensor capable of capturing multispectral images, including a UV light image; a processor configured to process the multispectral images to identify an area of interest; wherein the area of interest comprises a portion of a person's skin; wherein the processor is further configured to determine whether a portion of the area of interest lacks UV protection, and to render a display image from the multispectral images; wherein the display image indicates whether the portion lacks UV protection; and a display operable to display the display image. Further, the techniques can be implemented such that the processor is further configured to identify whether the portion lacks UVA protection and UVB protection. Further, the techniques can be implemented such that the determining comprises comparing one area of the UV light image to another area of the UV light image. Further, the techniques can be implemented to include a light source operable to provide UV light to the area captured by the one or more image sensors.

Various implementations of the subject matter described herein may provide one or more of the following advantages. In one or more implementations, the techniques, materials, compounds, and systems described herein can capture, process, and display images representing multispectral light, including the relative reflection and absorption of UV light relative to an object. Additionally, in one or more implementations, the techniques, materials, compounds, and systems described herein can identify one or more areas at risk of UV overexposure and can modify images to identify such areas. Accordingly, in one or more implementations the techniques, materials, compounds, and systems described herein can provide UV exposure context information particular to UV characteristics or individuals.

These general and specific techniques can be implemented using an apparatus, a method, a material, a compound, a system, or any combination of apparatuses, methods, materials, compounds, and systems. The details of one or more exemplary implementations are set forth in the accompanying drawings and the description below. Further features, aspects, and advantages of the disclosed implementations will become apparent from the description, the drawings, and the claims.

BRIEF DESCRIPTION OF THE DRAWINGS

FIG. 6 shows an exemplary multispectral image capture and processing device.

DETAILED DESCRIPTION

Figure 1:
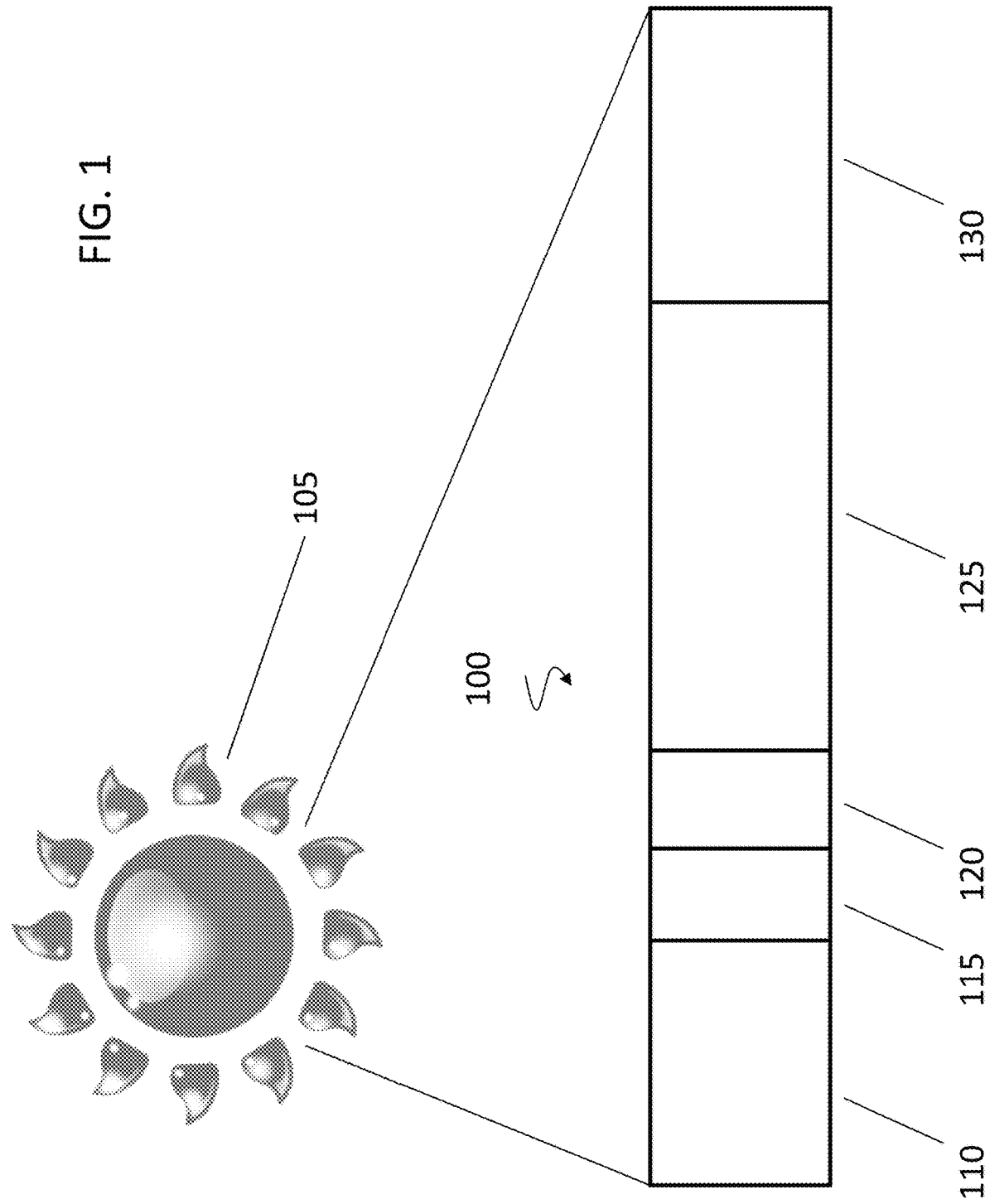
FIG. 1 shows a solar radiation spectrum.
Figure 2:
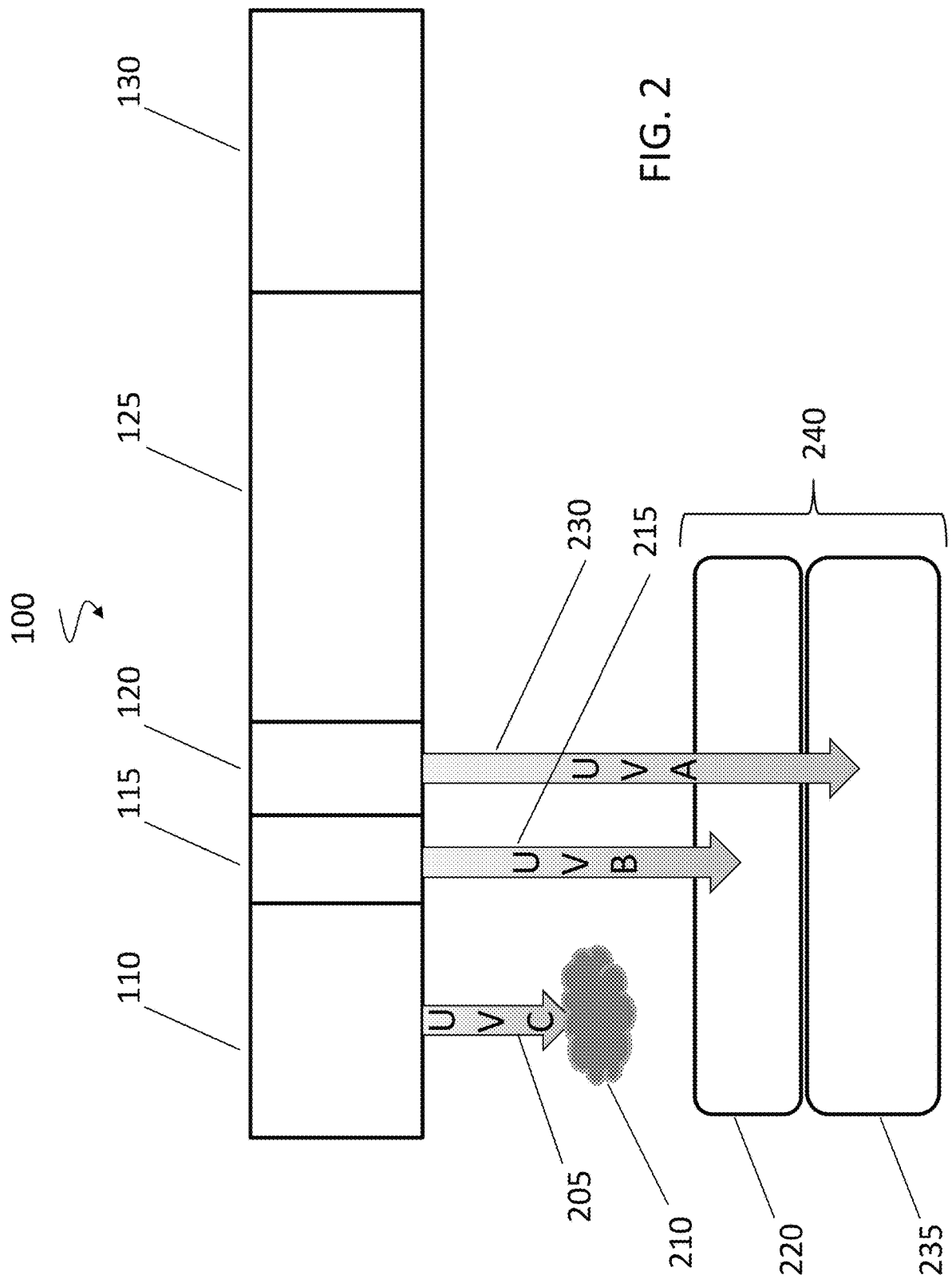
FIG. 2 shows the transmission and absorption of UV light.
Figure 3:
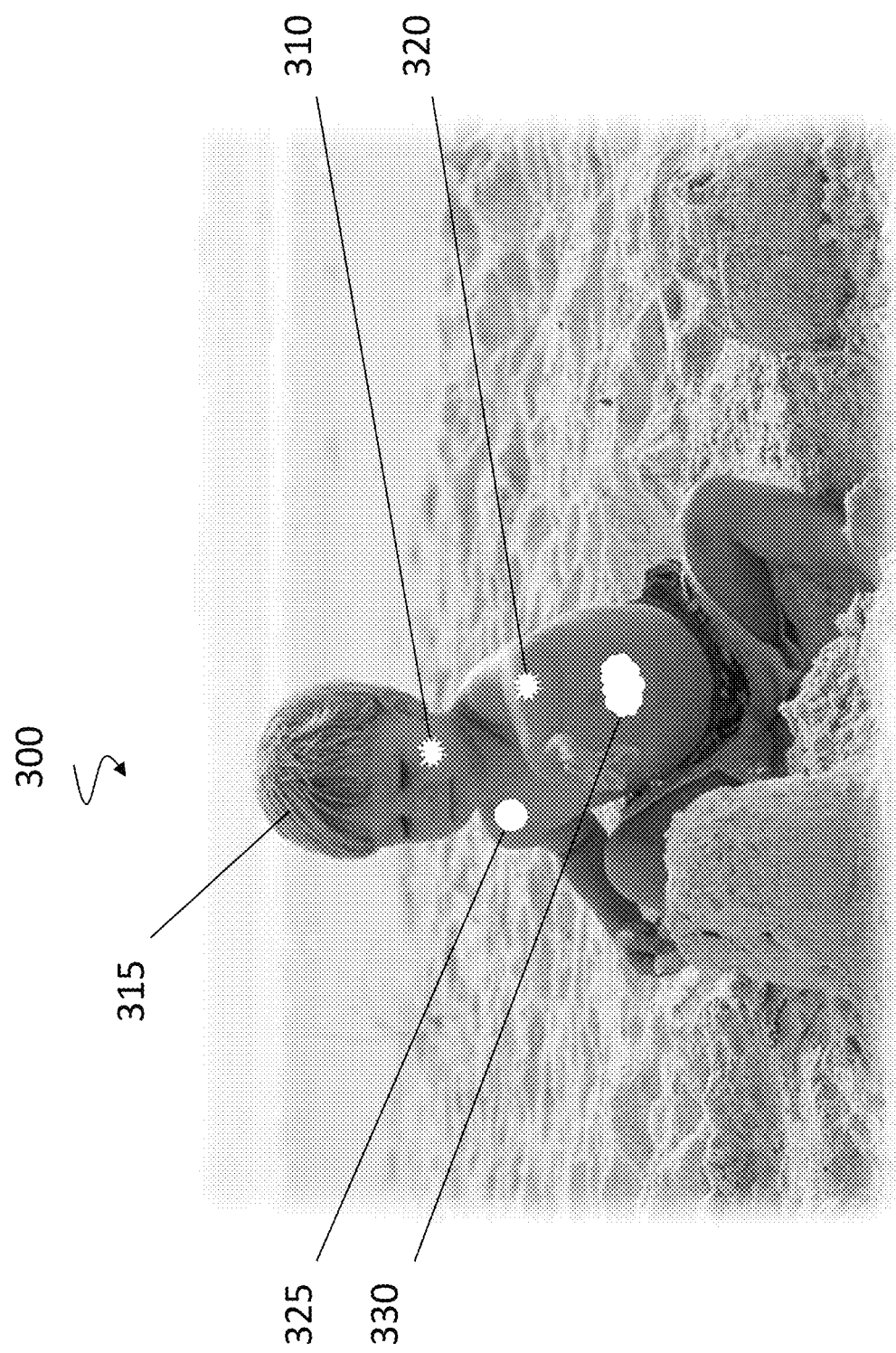
FIG. 3 shows coverage problems associated with sunscreen.
Figure 4:
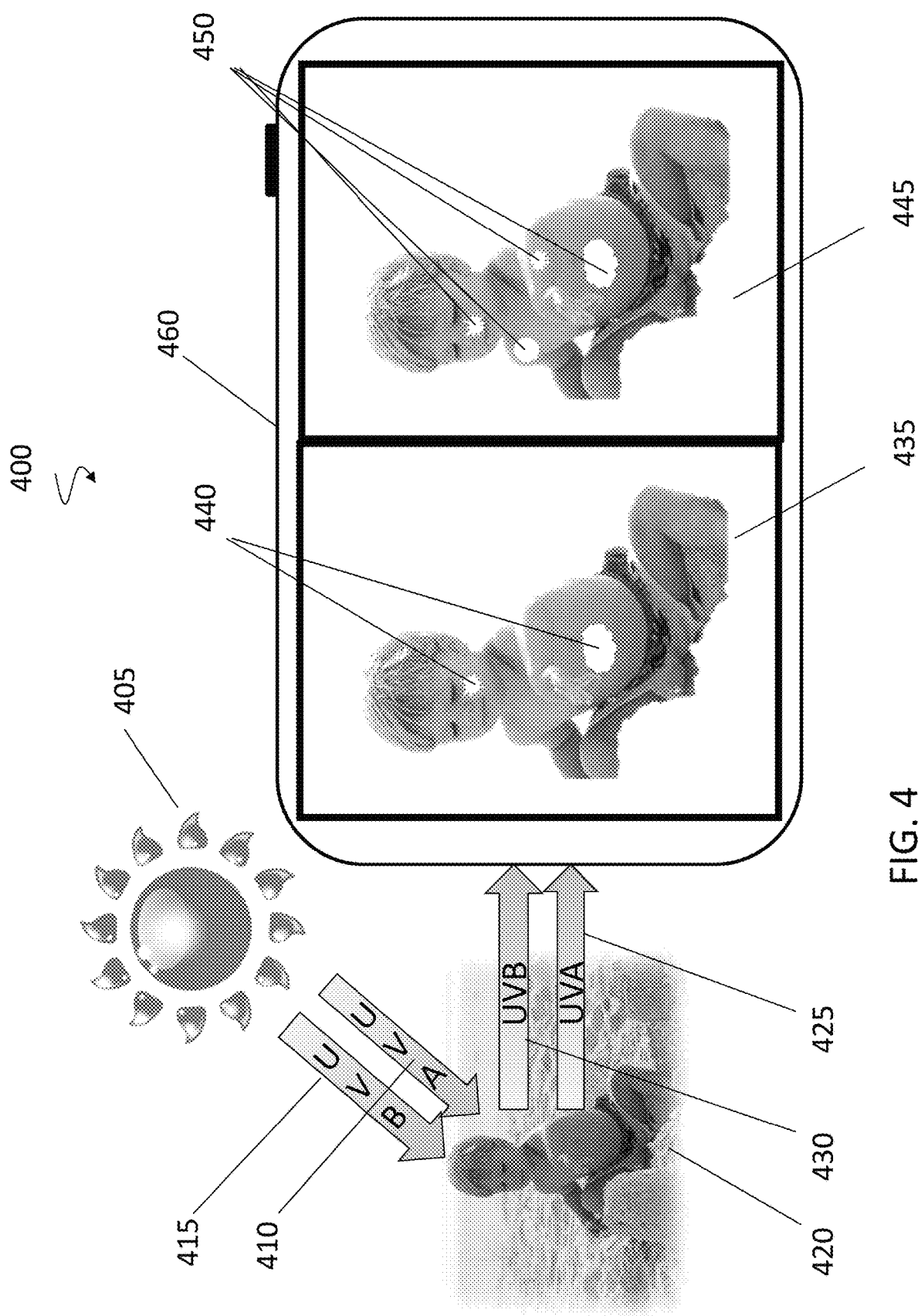
FIG. 4 shows an exemplary multispectral image capture and processing environment.

FIG. 4 shows an exemplary multispectral imaging capture and processing environment 400. The Sun 405 emits UVA 410 and UVB 415 light incident onto a boy 420. When the UVA 410 and UVB 415 light contacts the boy 420, some portion of the UVA 410 and UVB 415 light is absorbed and some portion is reflected as reflected UVA 425 and reflected UVB 430 light. Image capture device 460 captures at least a portion of the reflected UVA 425 light and the reflected UVB 430 light, and converts the captured, reflected light into electronic signals. Reflected UVB 430 light, which is invisible to the human eye, can be represented using one or more false colors as UVB image 435. Further, reflected UVA 425 light, which also is invisible to the human eye, is represented using one or more false colors as UVA image 445. The image capture device 460 also can capture full-color images. In some implementations, either or both of UVA image 445 and UVB image 435 can be overlaid on a full-color image. Areas of interest 440 and 450 show where UVB and UVA protection is lacking. In some other implementations, one or more UVA images and/or one or more UVB images can be at least partially combined with one or more images representing at least a portion of the visible light spectrum, e.g., to form a composite image.

Figure 5:
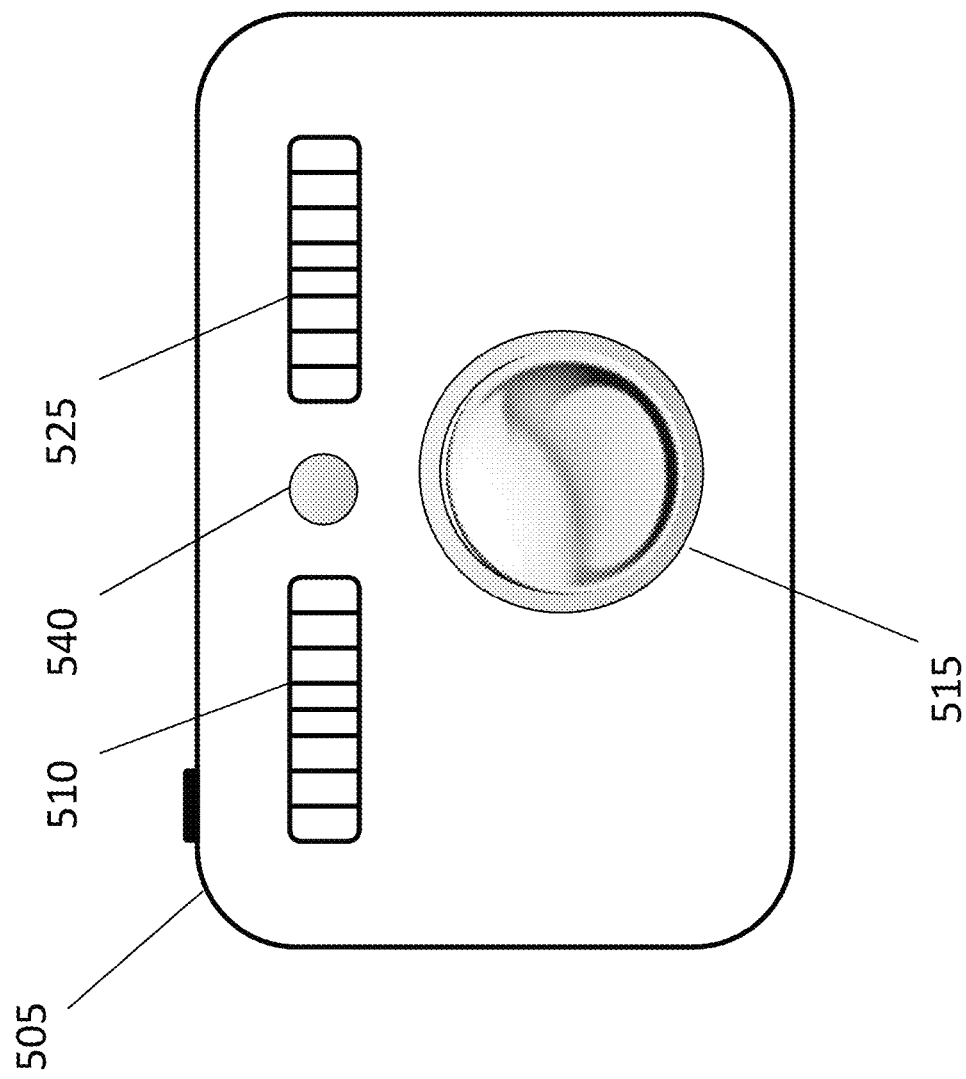
FIG. 5 shows an exemplary multispectral image capture and processing device.

FIG. 5 shows an exemplary multispectral image capture and processing device 505. Multispectral image capture and processing device 505 can have one or more UV light sources, such as light source 510. Light source 510 can be configured to provide UV light in one or more momentary flashes or persistently. Light source 510 also can be configured to provide only UVA light, only UVB light, only infrared light, a combination of UVA and UVB light, or a combination of all three. Multiple light sources can be used in combination, such as one or more UVA only light sources and one or more UVB only light sources. The multiple light sources also can be configured to emit light in any sequence, e.g., such that UVA light, UVB light, and infrared can be emitted either separately or simultaneously. Image capture and processing device 505 also can include an auto-focus assist lamp 540 that assists device 505 in better auto focus in the UVA, UVB, infrared or visible light spectrums by emitting infrared or UV light in low light situations. Image capture and processing device 505 also can have one or more visible-light sources, such as visible-light source 525 that can be configured to provide one or more momentary flashes or a persistent light.

Image capture and processing device 505 can include lens and sensor assembly 515. In a first formation, lens and sensor assembly 515 can include a sensor that separately captures UVA and UVB light. Lens and sensor assembly 515 can use a color-filter array (e.g. Bayer filter) or layered sensor stack (e.g. Foveon sensor). Lens and sensor assembly 515 can also capture visible light, and infrared light. In a second formation, lens and sensory assembly 515 can separate UVB, UVA, blue, green, red, and/or IR using a prism, such as a dichroic prism, and each spectrum can be sent to a separate image sensor. In a third formation, image capture and processing device 505 can capture UVB, UVA, red, green, blue, and infrared light using multiple lenses, sensors, and filters. In a fourth formation, some traditional visible-light sensors, which has UV sensitivity, can be used with a physical filter that blocks visible-light and only allows UV light to pass through the filter. Any UV-blocking filters on conventional visible-light sensors can be removed and the color-filter array can also be removed to increase sensitivity. Using these formations, image capture and processing device 505 can capture and store separate images for UVB, UVA, blue, green, red, and infrared.

FIG. 6 shows an exemplary multispectral image capture and processing device. Environment 600 includes image capture device 605. An image capture device can acquire UV, visible, and infrared light image information. An image capture device can also acquire UV intensity information over a period of time. An image capture device can also use location and other information to acquire additional UV-related information over a network, such as a UV index. An image capture device can receive information from a user. An image capture device can also process, analyze, and present this information in user interface that provides the user with awareness of UV characteristics.

Image capture device 605 can acquire UV, visible, and infrared light image information as discussed above with respect to capture and processing device 505. Image capture device 605 can use the image information to identify a user (e.g. a person), using face recognition, edge detection, motion detection, body outlines, infrared imaging, or other known means for identifying areas of interest. For example, image capture device 605 can identify a person as an area of interest, separate from a background, using face recognition and edge detection. As another example, if the user is close, image capture device 605 can use edge detection to outline the shape of a body part as an area of interest. Image capture device 605 can also display an outline on display 610 and display instructions prompting the user to place the area of interest inside the outline, and to indicate when the area of interest is there. For example, Display 610 could display an oval outline, representing a face, and ask the user to "please align the oval with the person's face."

Image capture device 605 can acquire UV intensity information over a period of time. Image capture device 605 can connect to a UV sensor, such as UV sensor 645, through a wired or wireless connection, such as connection 650. UV sensor 645 can be worn on the outside of clothing of a particular user, such as a swimsuit. Information from UV sensor 645 can be attributed to a user and stored as part of a user's UV profile. UV sensor 645 can obtain an absolute measure of incident UV on a user over time. For example, if the incident UV in the area is intense, but a user is in the shade, UV incident on that user is very low. Display area 640 can show UV incident information from a sensor, including incident UVA and UVB. Display area 640 can also show cumulative UV incident information over a period of time, such as the entire day. Display area 640 also can show user input information indicating the relative UV intensity over time. A user's exposure time can be predicted as discussed in U.S. Pat. No. 7,818,142, which is incorporated herein by reference.

UV intensity can depend on the date and time. UV intensity increases during the summer months when the sun is closer and during the early afternoon when the sun is at a more direct angle and the UV light has to pass through less of the Earth's atmosphere. A user can input the date and time into image capture device 605. Image capture device 605 also can obtain the date and time through a network connection. Image capture device 605 can connect to network 655, such as the Internet, through a connection, such as connection 660. Connection 660 can be wired or wireless.

Image capture device 605 can include a location sensor, such as a GPS sensor to identify the location. A user also can input location information into image capture device 605. Image capture device 605 can use location and other information to acquire additional UV characteristic information over a network, such as a UV index for a particular location or locations.

UV intensity can depend on several environmental, temporal, or location based information. Location information can indicate whether a user is closer to the equator and thus more likely to be exposed to strong UV. Location information can also indicate whether a user is close to reflective surfaces, such as water or snow, which can increase UV intensity. Location and temporal information can also be used to obtain weather information, such as whether it is cloudy or rainy, which can lower UV intensity. Location information can be used to obtain the altitude, where higher altitudes can increase UV intensity. Location and temporal information can further be used to obtain the UV Index, a prediction of UV intensity for a certain area. Image capture device 605 can obtain location based information (e.g. reflection, geography, UV index, weather) by looking up this information in an internal database, or through connection 660.

Image capture device 605 can include a display 610. Display 610 can accept user input, such as a touchscreen. Display 610 can show one or more captured images in area 620. A capture device can receive information from a user. A capture device can also process, analyze, and present this information in user interface that provides the user with awareness of UV characteristics. UV environment information, such as location-based information and time information, can be displayed in display area 635.

Image capture device 605 can be configurable to a particular user. A user can input user information into image capture device 605. As discussed above, image capture device 605 can also identify a user with face recognition. Image capture device 605 can create and store UV profiles containing UV information for users, such as each user's current UV exposure, historic UV exposure for a period of time, skin type, and images of prior UV exposure. Display area 665 shows information relating to a particular user's UV profile, such as the user's name (Chase), user's skin type (Fair), user's current UV exposure (OK), and the user's historical UV exposure (Poor). Image capture device 605 can also approximate a user's skin type based on the complexion in captured images.

UV exposure can be altered by applying sunscreen. A user can input the type of sunscreen by: taking a photo of the sunscreen container with image capture device 605, taking a photo of the ingredients, taking a photo of the UPC symbol on the sunscreen container with image capture device 605, a user inputting the name into image capture device 605, or a user inputting the active ingredients of the sunscreen into image capture device 605. Image capture device 605 can OCR the image of the ingredients, or process the UPC symbol to identify a particular type of sunscreen and then look up the active ingredients using an internal database or a network connection. Sunscreen types can be assigned to a user and multiple sunscreen types can be assigned to a user or multiple users. Image capture device 605 can display the sunscreen name, SPF/UVB rating, and UVA rating in display area 625. Image capture device 605 can user the active ingredients (chemical filters or physical filters) to interpret UV images captured by image capture device 605. For example, if the active ingredients include a UVA physical filter (reflecting UV) and UVB chemical filter (absorbing UV), the image capture device can interpret partial UV absorption as offering strong UV protection. If the active ingredients include only a chemical filter (absorbing), the image capture device can interpret partial UV absorption as offering weakened UV protection.

Current UV exposure can be displayed in areas 620 and 630. Display area 630 can contain a summary of the current measured UV exposure based on whether the current user is completely protected from UV in any captured images. Display area 620 can show problem areas for UVA, UVB or both, as described herein.

The environmental, sunscreen, incident, and measured information can be compiled to obtain a more complete picture of a user's UV exposure and risk. This information can be summarized in display area 665. For example, if the sunscreen in use is weak and the measured UV protection suggests the sunscreen has worn off, but the environment is low in UV or the UV sensor suggests the user has spent the day in the shade, image capture device 605 can indicate in display area 665 that current UV exposure is OK and the day's history of UV exposure is OK. Image capture device 605 can also provide stronger alerts, such as an audible sound or flashing screen, if a user is at risk for excessive UV exposure, UVA related sun damage, or sunburn. Image capture device 605 can also recommend a sunscreen based on the compiled data, such as skin type, UV exposure history, and environmental data.

FIG. 7 shows exemplary processed multispectral light images. For example, image capture device 400, 505, or 605 can process multispectral light images. Image capture devices can separately sense UV, red, green, blue, and infrared light. FIG. 7A shows an image rendered by an image capture device from UV light, UV image 710. UV light is invisible to the human eye, so UV image 710 can be rendered with one or more false colors or in black and white. Dark areas in UV image 710 can represent where UV is being absorbed and light areas can represent where UV is being reflected. Areas of interest 715 can indicate areas of interest where UV is being reflected above a threshold and thus not absorbed by a sunscreen using chemical filters. Areas of interest 715 can also represent areas where UV is being partially reflected above a threshold because the sunscreen also uses a physical filter that reflects UV, and thus those areas covered by the sunscreen would be darker than those areas not covered. As discussed below, a user can indicate to the image capture device whether a chemical filter, physical filter or both are being used. Alternatively, the image capture device can infer the type of filter based on the relative intensities of UV light on the majority of an individual and the surrounding environment. The image capture device can determine the areas of interest by comparing the amount of UV light in portions of the image identified as being human skin to a predetermined UV light threshold based on the reflectivity of chemical filters, physical filters, sunscreens, or a relative UV light threshold based on the reflectivity on portions of a person's skin relative to other portions of a person's skin and/or the surrounding environment. In yet another alternative, the image capture device can ask the user to identify a portion of an image that has sunscreen and use the intensities of UV light in that portion to determine the UV light threshold.

Figure 7B:
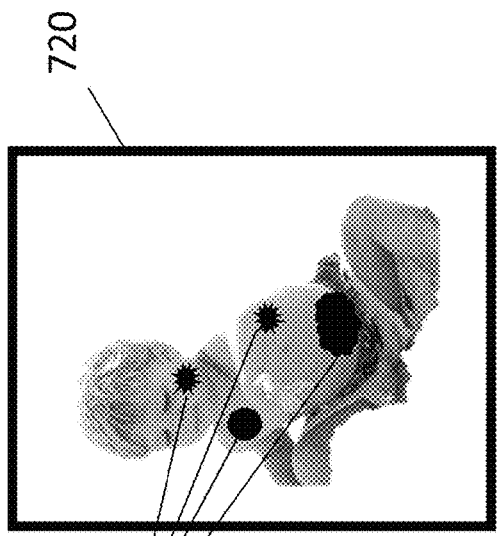
FIGS. 7A-7D show exemplary processed multispectral light images.
Figure 7A:
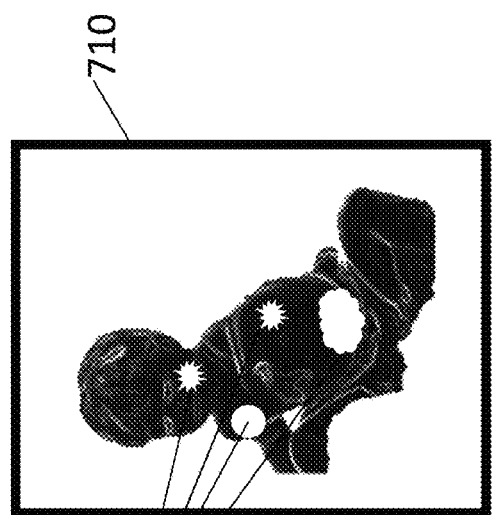

Because a sunscreen using chemical filters can absorb a significant amount of incident UV light, resulting in a darkened image, an image capture device can adjust the brightness and contrast to enhance viewing or an image capture device can at least partially composite the UV images with one or more visible light images. The one or more visible light images can be aligned with the UV images. The images, or portions of them, can be combined by making one or both of them partially transparent. FIG. 7B shows an image rendered by an image capture device from UV light and visible light, image 720. Areas of interest, identified by the image capture device as lacking sunscreen, areas 725, can be composited onto the visible light image using a false color, such as a bright orange. The image capture device can designate a fixed color to use as the false color for all photos, the user can select a false color, or the image capture device can select a false color that contrast with the visible light image (e.g. if the image has no orange, orange could be used as the false color.)

Figure 7D:
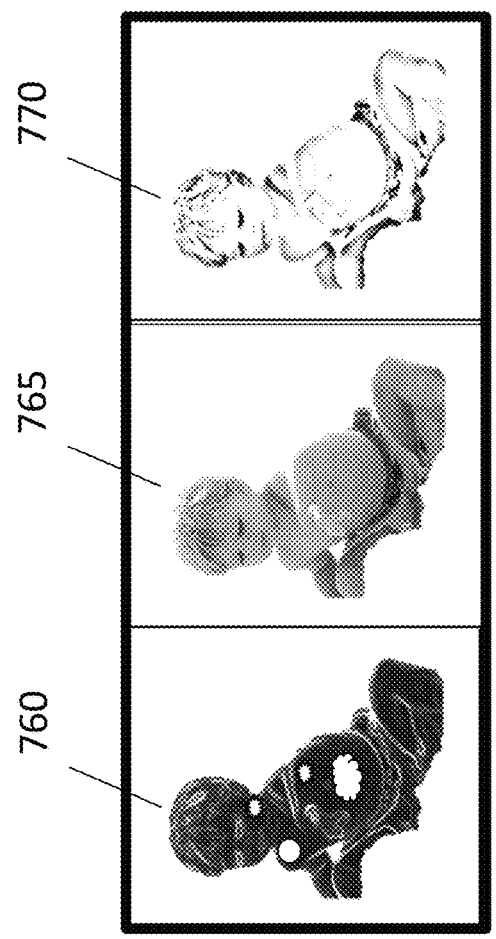
Figure 7C:
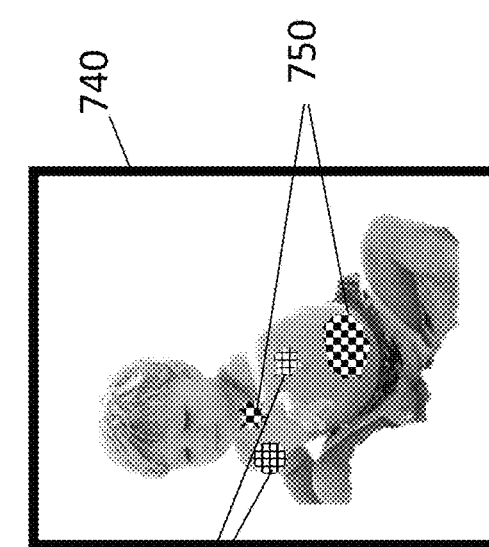

An image capture device can separately sense UVA, UVB, red, green, blue and infrared light. FIG. 7C shows an image rendered with an image capture device that can separately sense UVA and UVB light, UVA-B image 740. The UVA image data can be separately analyzed to determine UVA protection. Areas of interest 745 can indicate where UVA coverage is insufficient. The UVB image data can be separately analyzed to determine UVB protection. Areas of interest 750 can indicate where UVB is coverage is lacking. UVA and UVB problem areas can be identified using different false colors or patterns. The UVA and UVB data can be presented as separate images. By comparing UVA image data and UVB image data, an image capture device can determine when a sunscreen offers only UVB protection.

An image capture device can separately capture UVA, UVB, red, green, blue light, and infrared light. The separate images can be separately presented to a user. FIG. 7D shows separate images presented to a user side by side. Image 760 shows a UV image. Image 765 shows a visible light image. Image 770 shows an infrared image. UVA and UVB images could also be shown side by side.

The visible light image data can aid in performing edge detection, person detection, background detection, face detection, face recognition, clothing detection, skin type determination, or other analysis and rendering. An image capture device can analyze the UV image data (UVA image data, UVB image data or both) to perform edge detection, person detection, background detection, face detection, face recognition, clothing detection, skin type determination, and noise reduction. An image capture device can also analyze the UV image data to detect areas of interest 715, 745 and 750 using edge detection and relative intensities, and then enhancing those areas by making them brighter, drawing edges around them, or rendering them with a false color. Similarly, an image capture device can analyze infrared images that can aid in edge detection, person detection, background detection, face detection, clothing detection, and other analysis.

An image capture device can use different colors to represent the quality of UV coverage. For example, the image capture device can evaluate the UV data and render areas of interest on a person in green if UV protection is strong, yellow if it is weak, or red if it is absent. Additionally in a "fun mode" designed for kids, the kid could "color" themselves with a selected color or rainbow stripes by applying sunscreen, effectively turning the application of sunscreen into a game.

An image capture device can also perform 3-D analysis and renders. A user can spin in front of the image capture device, creating a series of composite images that the image capture device can stitch together to create a 3-D composite of a user, with UVA and UVB areas of interest indicated on the 3-D composite. The image capture device can allow the user to turn and manipulate the 3-D composite to see all the problem areas. Alternatively, the image capture device can use an icon (e.g. a stick figure) to represent the individual and mark problem spots on the icon.

Figure 8:
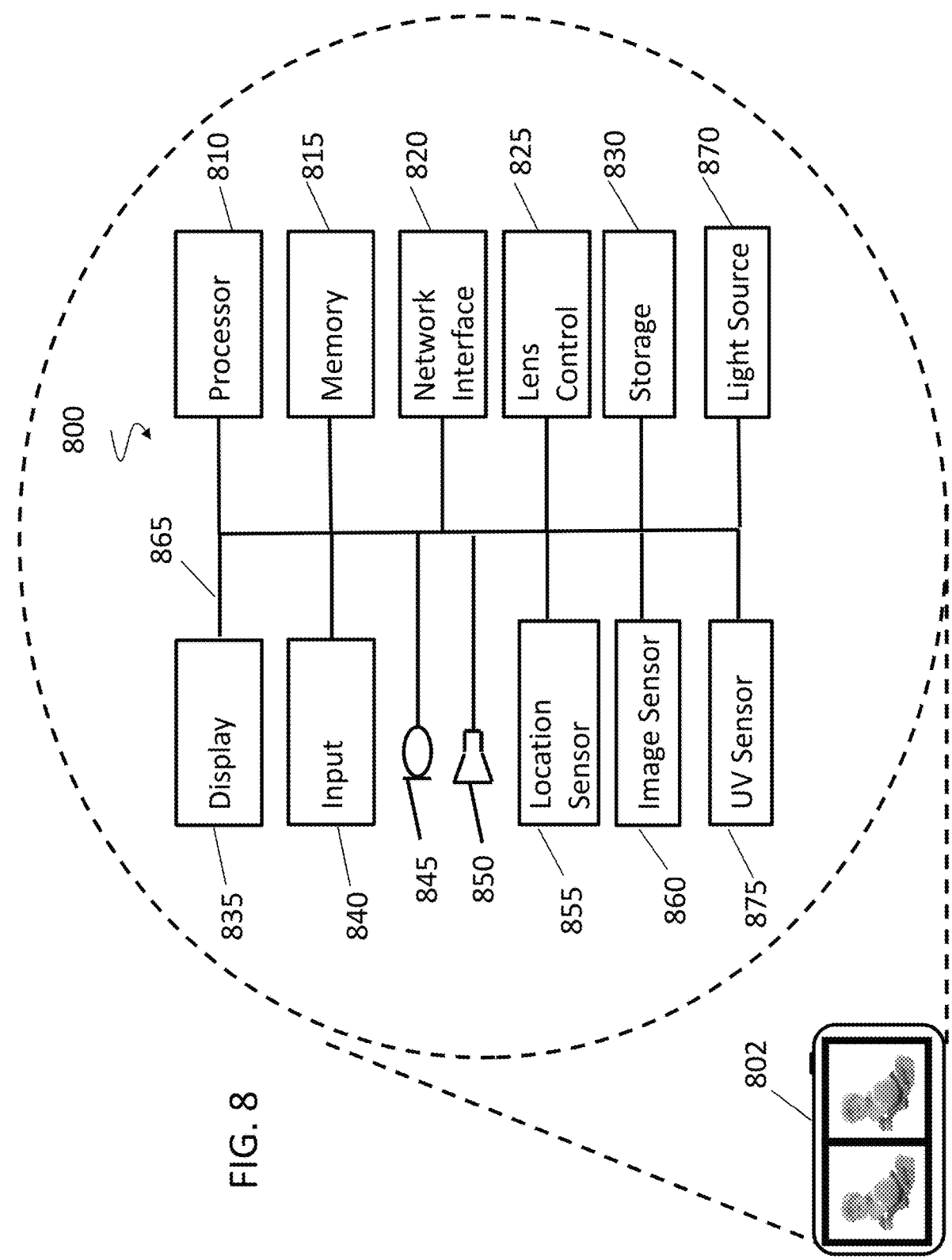
FIG. 8 shows a block diagram of an exemplary multispectral image capture and processing device.

FIG. 8 shows a block diagram of an exemplary multispectral image capture and processing device. FIG. 8 presents a computer system 800 that can be used to implement the techniques described herein for sharing digital media. The computer system 800 can be implemented inside of image capture device 802 (e.g. 400, 505 and/or 605). The computer system 800 can include an image sensor 860 for receiving UV and visible light, and converting them into an image signal. Alternatively, image sensor 860 can be comprised of multiple sensors that each receive and sense different wavelengths, such as UVA, UVB, red, green, blue, and/or infrared light. Image sensor 860 can be coupled to bus 865, which can be used to transfer the image signal to one or more additional components. Lens control 825 can control the operation of a lens assembly, including zoom, autofocus, and exposure settings. Bus 865 can include one or more physical connections and can permit unidirectional or omnidirectional communication between two or more of the components in the computer system 800. Alternatively, components connected to bus 865 can be connected to computer system 800 through wireless technologies such as Bluetooth, Wifi, or cellular technology.

Computer system 800 can include light source 870 that produces UV light (e.g. using a Wood's lights, gas-discharge lamps, ultraviolet LEDs), visible light, and/or infrared light. The computer system 800 can include a microphone 845 for receiving sound and converting it to a digital audio signal. The microphone 845 can be coupled to bus 865, which can transfer the audio signal to one or more other components. The computer system 800 can include a UV sensor 875 for determining the intensity of incident UV light. UV sensor 875 can include multiple sensors assigned to different users and attached to their clothing to monitor exposure through a day or longer. Computer system 800 can further include a location sensor 855 for detecting the relative or absolute position of computer system 800. Location sensor 855 can use GPS, assisted-GPS, GSM localization, or similar technologies.

An input 840 including one or more input devices also can be configured to receive instructions and information. For example, in some implementations input 840 can include a number of buttons. In some other implementations input 840 can include one or more of a mouse, a keyboard, a touch pad, a touch screen, a joystick, a cable interface, and any other such input devices known in the art. Further, audio and image signals also can be received by the computer system 800 through the input 840.

Further, computer system 800 can include network interface 820. Network interface 820 can be wired or wireless. A wireless network interface 820 can include one or more radios for making one or more simultaneous communication connections (e.g., wireless, Bluetooth, cellular systems, PCS systems, or satellite communications). A wired network interface 820 can be implemented using an Ethernet adapter or other wired infrastructure.

An audio signal, image signal, user input, metadata, other input or any portion or combination thereof, can be processed in the computer system 800 using the processor 810. Processor 810 can be used to perform analysis, processing, editing, playback functions, or to combine various signals. For example, processor 810 also can perform facial recognition and assign information such as exposure time, skin type, or UV intensity to a user based on facial recognition. Processor 810 can analyze an image signal to determine the outline of an individual, identify clothing, and determine a person's skin type. Processor 810 can use memory 815 to aid in the processing of various signals, e.g., by storing intermediate results. Memory 815 can be volatile or non-volatile memory. Either or both of original and processed signals can be stored in memory 815 for processing or stored in storage 830 for persistent storage. Further, storage 830 can be integrated or removable storage such as Secure Digital, Secure Digital High Capacity, Memory Stick, USB memory, compact flash, xD Picture Card, or a hard drive.

The image signals accessible in computer system 800 can be presented on a display device 835, which can be an LCD display, printer, projector, plasma display, LED, OLED, or other display device. Display 835 also can display one or more user interfaces such as an input interface. The audio signals available in computer system 800 also can be presented through output 850. Output device 850 can be a speaker or a digital or analog connection for distributing audio, such as a headphone jack.

Figure 9:
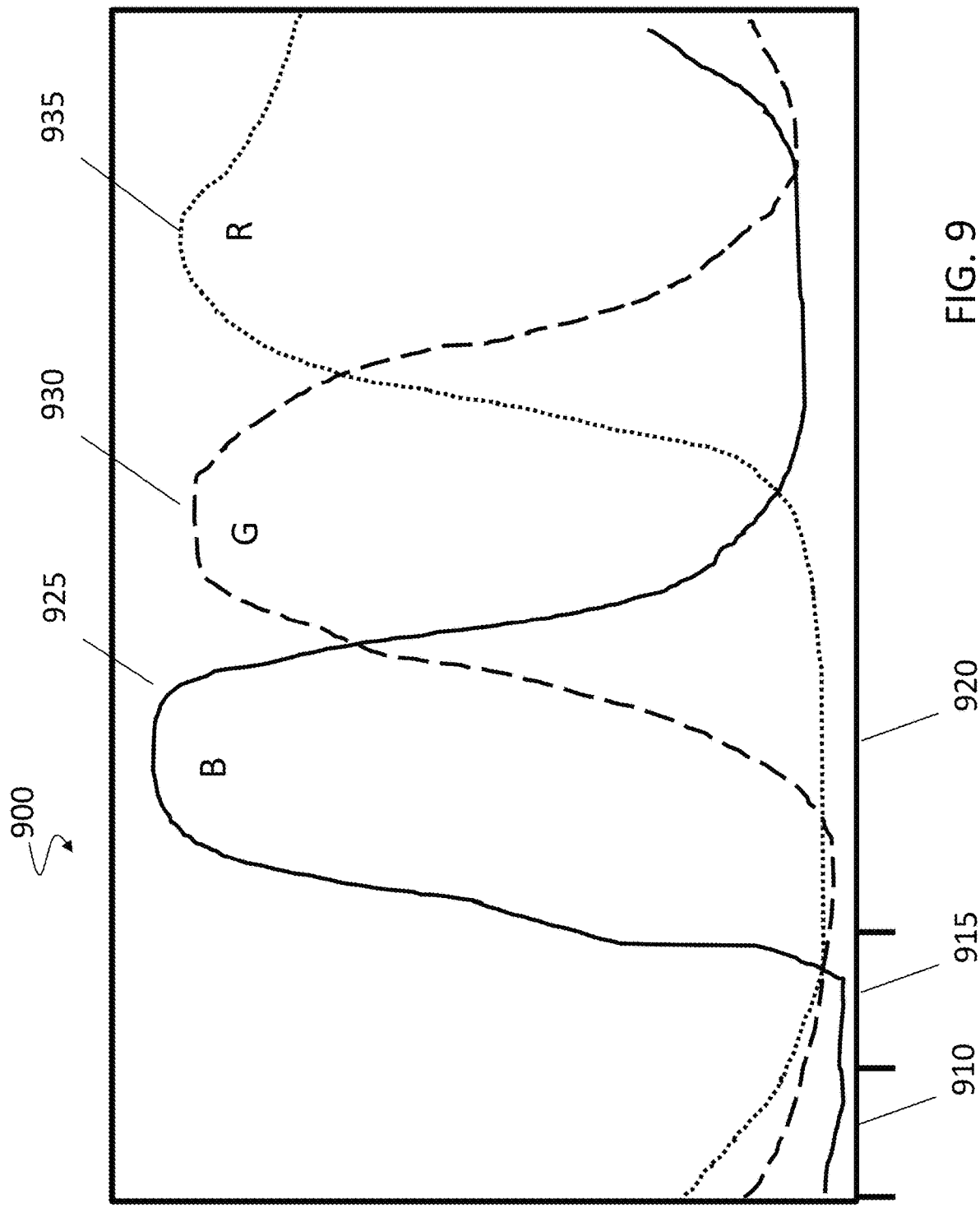
FIG. 9 shows sensitivities of an exemplary digital camera sensor in red, green, and blue channels.

FIG. 9 shows the sensitivities of an exemplary digital camera sensor in its red, green, and blue channels. Traditional CCD and CMOS sensors are known to have sensitivity in the UV spectrum. CCD and CMOS color sensors can have separate "channels" that measure the blue, green, and red in the incoming light. Sensitivity diagram 900 shows the sensitivity (y-axis) of the red, green, and blue channels of a sensor across various wavelengths (x-axis). Region 910 shows the UVB wavelengths. Region 915 shows the UVA wavelengths. Region 920 shows the visible light wavelengths. Blue-response curve 925 shows the sensitivity of a blue channel across the UVB, UVA, and visible wavelengths. Green-response curve 930 shows the sensitivity of a green channel across the UVB, UVA, and visible wavelengths. Red-response curve 935 shows the sensitivity of a red channel across the UVB, UVA, and visible wavelengths. The red channel and green channels show sensitivity for UVA light, and thus can be used to capture UVA light. The red and green channels also show sensitivity for UVB light, and thus can be used to capture UVB light. A UV-pass filter can be applied in front of the sensor represented by sensitivity diagram 900 to block the visible light so the sensor will only receive UVA and UVB light. Alternatively, a single sensor can have an additional separate channel that captures UV light.

In yet another alternative, one sensor can be used for visible light, another sensor for UVA, and another for UVB light. The visible light, UVA, and UVB can be separate from the incoming light using a prism or similar known methods.

Figure 10:
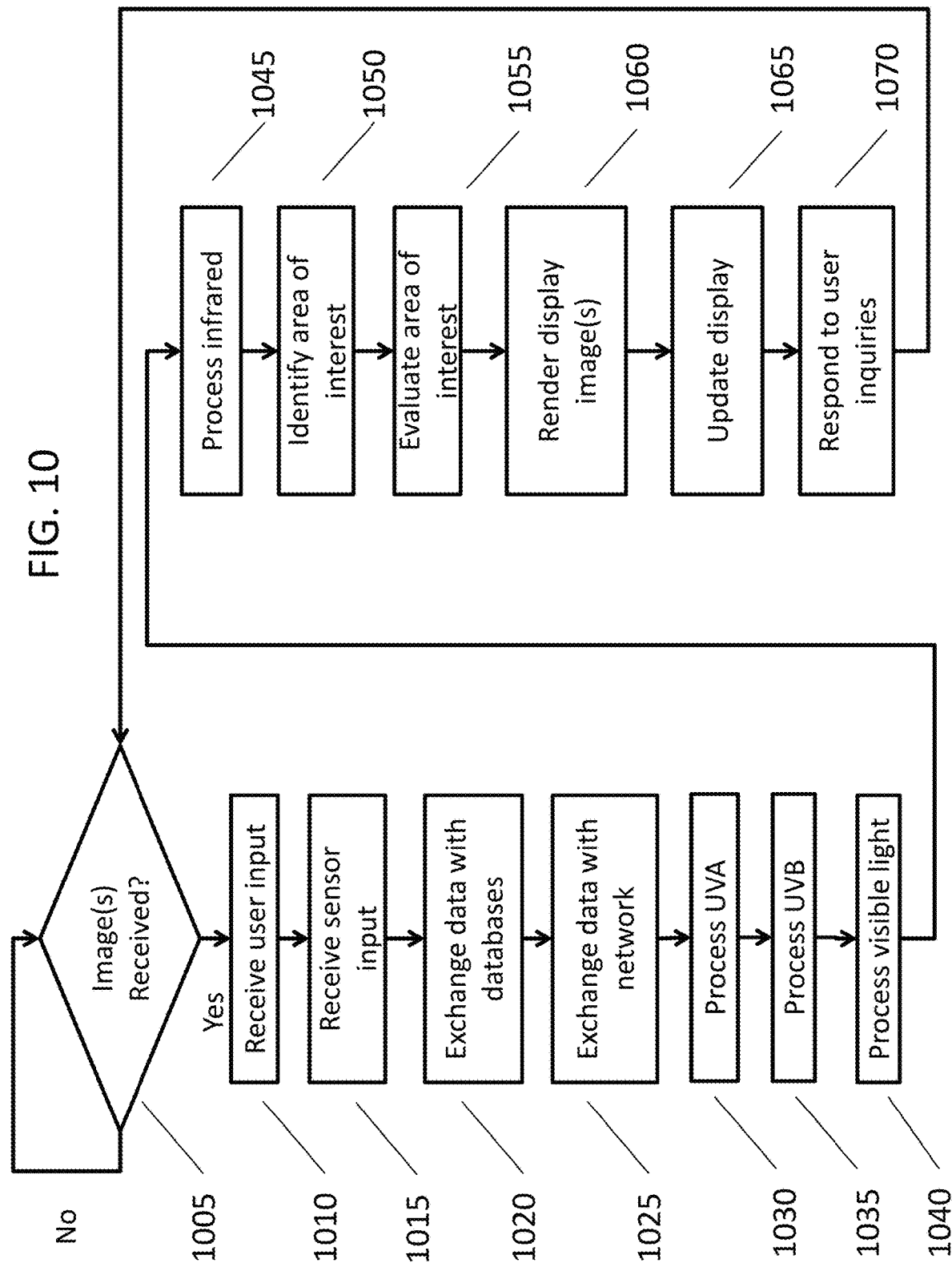
FIG. 10 shows exemplary steps for processing captured ultraviolet light.

FIG. 10 shows exemplary steps for processing captured multispectral light. An image capture device can monitor an image sensor until images are received (1005). If no images are received, the image capture device can continue to monitor its sensor until images are received (1005). The image capture device can receive user input (1010). User input can include information regarding the type of sunscreen in use, location, user identification, skin type, or other information identified herein. The image capture device can receive sensor input (1015). Sensor input can include location information, such as location information, UV sensor information, or other information discussed herein. The image capture device can exchange the sensor or user data with databases (1020) and/or a network (1025). For example, the image capture device can provide location and time information to the network and receive UV Index, weather, location name, and general UV intensity information.

The image capture device can process UVA image information (1030), and UVB image information (1035). Processing UVA image information (1030) and UVB image information (1035) can include comparing images captured at one moment in time with another. The UVA and UVB image information can be combined when received, kept separate, or both. Processing UVA image information (1030) and UVB image information (1035) an include motion detection, face detection, person detection, background detection, edge detection, and exposure adjustments. Processing UVA image information (1030) and UVB image information (1035) can include making contrast, brightness, local contrast, and saturation enhancements, as well as creating high dynamic range images from multiple images.

The image capture device can process visible light image information (1040). Processing visible light image information (1040) can include comparing images captured at one moment in time with another. Processing visible light image information (1040) can include processing red, green, and blue light. The visible light image information can be black and white. Processing visible light image information (1040) can include face detection, motion detection, person detection, edge detection, exposure adjustments, and determining which portions of persons are bare skin. Processing visible light image information (1040) can include making contrast, brightness, local contrast, and saturation enhancements, as well as creating high dynamic range images from multiple images.

The image capture device can process infrared light image information (1045). Processing infrared light information (1045) can include comparing images captured at one moment in time with another. Processing infrared light information image (1045) can include face detection, person detection, edge detection, exposure adjustments, and determining which portions of persons are bare skin. Processing infrared light image information (1045) can include making contrast, brightness, local contrast, and saturation enhancements, as well as creating high dynamic range images from multiple images.

The image capture device can identify areas of interest (1050). The areas of interest can be identified using UVA and UVB light images, as well as visible light images, and/or infrared light images. The areas of interest can be identified (1050) using enhanced or unenhanced versions of those images, as well as multiple images of the same type. Identifying areas of interest (105) can include using analysis performed on separate UV, visible light, and infrared light image information, or composites created from portions of some or all of those images, including edge detection, person detection, background detection, face detection, face recognition, clothing detection, skin type determination. Identifying areas of interest (1050) can include identify users or portions of users with exposed skin. The image capture device can evaluate areas of interest (1055).

Evaluating areas of interest (1055) can include determining which portions of bare skin are not covered by UVA and/or UVB protective materials or compounds, and/or determining the strength of UVA and UVB protection. Evaluating areas of interest (1055) can include comparing prior UVA and UVB images. Evaluating areas of interest (1055) can factor in, among other things, a UV light threshold based on the type of sunscreen and active ingredients in the sunscreen being used. Evaluating areas of interest (1055) also can factor in, among other things, a UV light threshold based on the relative intensities in the areas of interest and/or outside the areas of interest. Evaluating the areas of interest (1055) also can factor in sensor data and environmental data such as UV index, UV intensity, weather, skin type, and other UV-influencing factors discussed herein.

The image capture device can also render images for display (1060). Rendering display images (1060) can include a composite of UVA, UVB, visible light, and/or infrared light images and/or portions of the images overlaid on top of each other. Rendering display images can include making enhancement to the original or composite images, such as contrast, brightness, local contrast, and saturation enhancements, as well as creating high dynamic range images from multiple images. Rendering display images (1060) can include false colors for UVA, UVB, infrared images, and/or portions of those images. Rendering display images (1060) can overlay colors indicating areas of interest where UVA and/or UVB coverage is lacking. Rendering display images (1060) can indicate UVA and/or UVB coverage using separate colors or indicators. Rendering display images (1060) can be a view of a 3-D composite image. The rendering of display images (1060) can include designating areas lacking in UVA and UVB with one or more icons or patterns. The rendering of display images (1060) can include information for the user, such as sunscreen information, environment information, user-specific information, UV coverage measures, measures of UV incident light, and other information disclosed herein. The image capture device can render display images (1060) including warnings or other indicators if sunscreen coverage is lacking such that a user can be harmed. The image capture device can update the display with rendered images (1065).

The image capture device can respond to user inquiries (1070). For example, a user may touch an area identified as lacking UVA or UVB coverage and the image capture device can respond with additional information, indicating if the area lacks UVA or UVB, or how long an area has been lacking coverage based on prior images. The image capture device can then wait for additional images (1005).

The steps described in FIG. 10 need not be performed in the order recited and two or more steps can be performed in parallel. In some implementations, other types of multispectral information or multispectral information can be processed, rendered and displayed.

Figure 11:
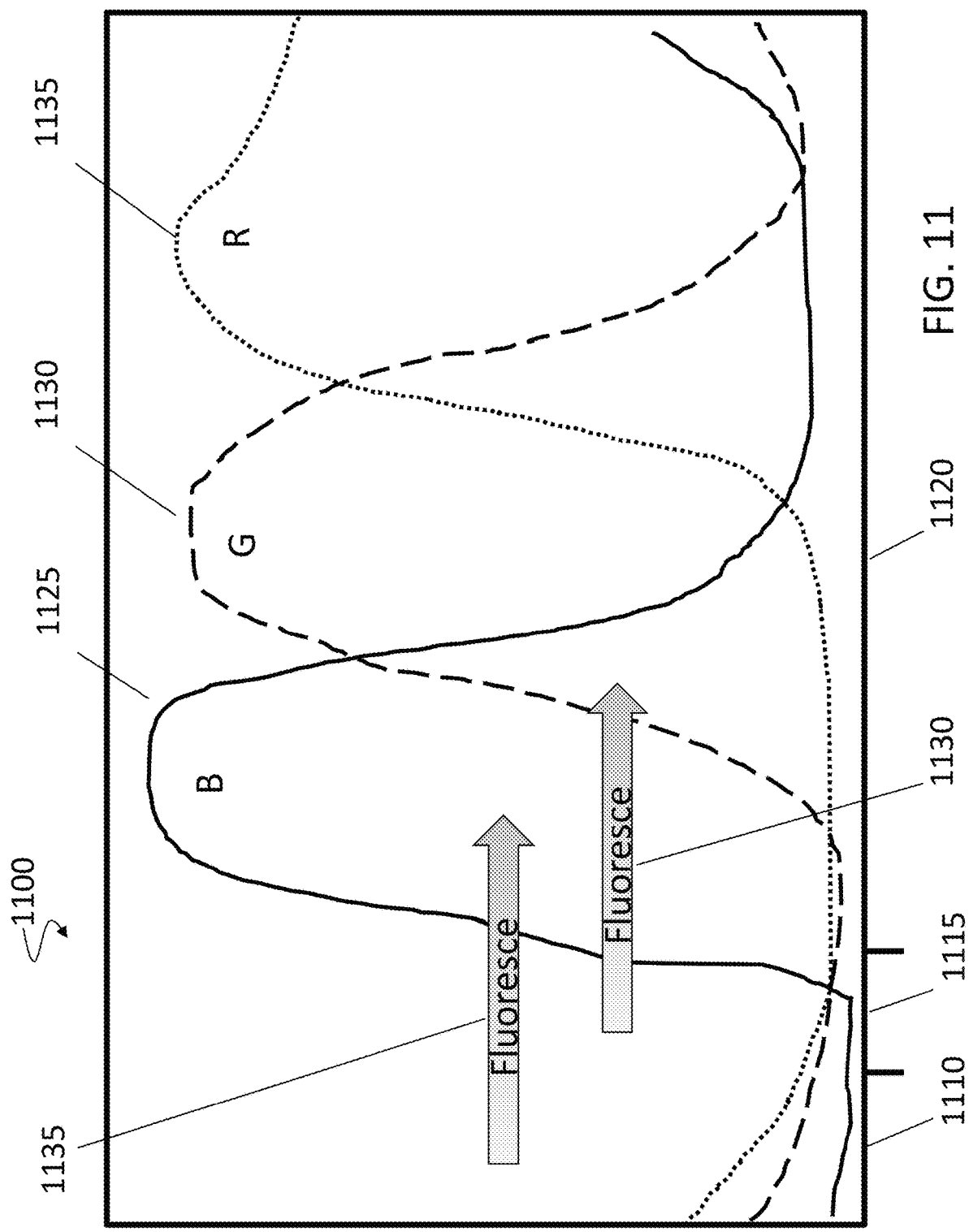
FIG. 11 shows an example of fluorescent materials shifting light into frequencies of a traditional camera sensor.

FIG. 11 shows an example of fluorescent materials shifting light into frequencies of a traditional camera sensor. In another example, fluorescing materials can be inserted into a topical compound, such as sunscreen, that absorbs UV light and emits light of a different frequency. The emitted light can be detected by an image sensor. Areas with the fluorescing materials will be brighter than those without, allowing a user to differentiate between areas where the topical compound is present and where it is not by looking at the image captured by the image sensor. The fluorescent image can also be analyzed, processed, and displayed as discussed above for UV images. Further, the fluorescing material can allow the sunscreen to remain mostly or completely invisible to the human eye, yet detectable with a typical image sensor.

Sensitivity diagram 1100 shows the sensitivity (y-axis) of the red, green, and blue channels of an image sensor across various wavelengths (x-axis). Region 1110 shows UVB wavelengths. Region 1115 shows UVA wavelengths. Region 1120 shows the visible light wavelengths. Blue-response curve 1125 shows the sensitivity of a blue channel across the UVB, UVA, and visible wavelengths. Green-response curve 1130 shows the sensitivity of a green channel across the UVB, UVA, and visible wavelengths. Red-response curve 1135 shows the sensitivity of a red channel across the UVB, UVA, and visible wavelengths.

Fluorescing materials can absorb UVA and emit light at a longer wavelength 1130. Fluorescing materials can also absorb UVB and emit light at a longer wavelength 1135. Longer wavelengths 1130 and 1135 can be the same or different. The fluorescing materials used for UVA and UVB can be the same or different. The fluorescing materials for UVA can be configured to emit into a wavelength of one of the red, green, or blue channels, while the fluorescing materials for the UVB can be configured to emit into a different channel. A filter can be applied in front of the sensor represented by sensitivity diagram 900 so the sensor will only receive either of the longer wavelengths (allowing to separately sense UVA or UVB) or both, but not other wavelengths. The longer wavelengths can be visible to the human eye (e.g. 400-700 nm) or shorter than visible light but still in a range of high sensitivity (e.g. 350-400 nm).

The previously described apparatuses (e.g. capture and processing devices) and methods can also be used to process the fluorescent images. As an example, flourescing materials can be used to enhance the UV images captured by the previously described apparatuses by emitting at a wavelength that matches the sensitivity of the UV image sensors.

Figure 12:
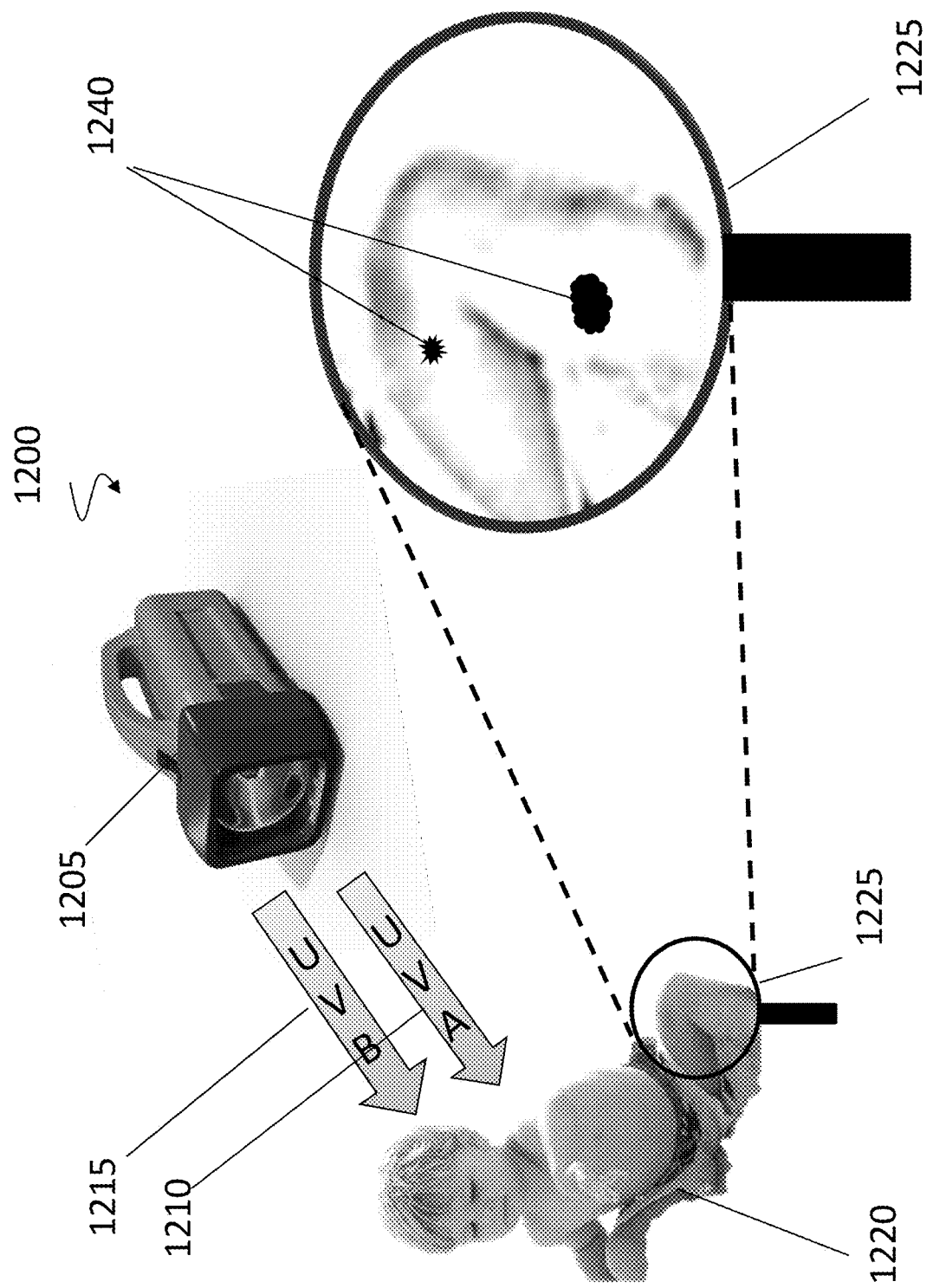
FIG. 12 shows an exemplary fluorescing environment.
Like reference symbols indicate like elements throughout the specification and drawings.

FIG. 12 shows an example of a fluorescing environment 1200. In yet another example, fluorescing materials can be inserted into a topical compound, such as sunscreen, that absorbs UV light and emits light of a different frequency. The emitted light can be detected by a user using a filter to block out all other wavelengths. Areas with the fluorescing materials will be brighter than those without, allowing a user to differentiate between areas where the topical compound is present and where it is not. Further, the fluorescing material can allow the sunscreen to remain mostly or completely invisible to the human eye, yet detectable with a filter and without additional equipment.

Light source 1205 can produce UVA 1210 and UVB 1215 light. Boy 1220 is playing. Boy 1220's sunscreen includes fluorescing material. Filter 1225 can block out all wavelengths except that emitted by the fluorescing material. By holding filter 1225 over boy 1220, a user can see spots 1240 where less fluorescent light is being emitted because there is little or no sunscreen in that location. Filter 1225 can integrate light source 1205 into it so that one device can be used to emit sufficient UV light for the fluorescent material to emit at a sufficient brightness for a user to see the light through the filter. Filter 1225 can also be a pair of goggles or glasses. Light source 1205 can also include the sun.

In another embodiment, the inventions disclosed herein can identify areas of hyperpigmentation and using historical images, identify triggering events.

In another embodiment, the inventions disclosed herein can be used to monitor the application, absorption, and degradation of topical compounds (e.g. medicines, lotions, soaps, sunless tanning lotions or sprays) that inherently interact with ultraviolet light.

In another embodiment, the inventions disclosed herein can be used to insert UV-interactive compounds such as chemical filters and/or physical filters to monitor the application, absorption, and degradation of topical compounds (e.g. medicines, lotions, soaps, sunless tanning lotions or sprays) that interact with ultraviolet light.

A number of implementations have been disclosed herein. Nevertheless, it will be understood that various modifications can be made without departing from the spirit and scope of the claims. Accordingly, other implementations are within the scope of the following claim.

What is claimed is:

1. A mobile device comprising:
a camera sensor system capable of capturing a multispectral image comprising representations of wavelengths of light in a visible spectrum and an ultraviolet spectrum;
a computer system coupled to the camera sensor system and configured to process the multispectral image to detect and identify an area representing a user in the multispectral image;
the computer system is further configured to identify one or more areas of interest of the area representing the user by comparing the area representing the user with a predetermined-ultraviolet-light threshold;
the computer system is further configured to render a display image for display from the multispectral image; wherein the rendering indicates the identified one or more areas of interest; and
a display coupled to the computer system and operable to display the rendered display image at approximately the same time the multispectral image is captured; and
wherein the camera sensor system is further capable of separately capturing ultraviolet A wavelengths and ultraviolet B wavelengths,
the computer system is further configured to separately identify whether the identified one or more areas of interest lacks ultraviolet A protection and ultraviolet B protection; and
the computer system is further configured, when rendering the display image, to assign different false colors to the identified one or more areas of interest that lack ultraviolet A protection and the identified one or more areas of interest that lack ultraviolet B protection.

2. The mobile device of claim 1, wherein the predetermined-ultraviolet-light threshold is based on an ultraviolet reflectivity of a topical compound comprising sunscreen.

3. The mobile device of claim 1, wherein the predetermined-ultraviolet-light threshold is based on an ultraviolet reflectivity of a portion of the area representing a user n the multispectral images to (i) another portion of the portion of the area representing a user in the multispectral images or (ii) an area outside the portion of the area representing a user in the multispectral images.

4. The mobile device of claim 1, wherein the camera sensor system uses an optical filter on a lens to filter out visible light.

5. The mobile device of claim 1, further comprising: means to obtain information comprising a type of sunscreen; means to obtain an ultraviolet characteristics of that type of sunscreen; and wherein the computer system is further operable to use the ultraviolet characteristics to set the predetermined-ultraviolet-light threshold.

6. The mobile device of claim 1, wherein the camera sensor system is further capable of capturing wavelengths of light in an infrared spectrum; and the computer system further configured to identify the area of interest using the wavelengths of light in the infrared spectrum.

7. The mobile device of claim 1, further comprising an ultraviolet sensor capable of determining an intensity of incident ultraviolet light; wherein the predetermined-ultraviolet-light threshold is based on the intensity of incident ultraviolet light.

8. A mobile device comprising:
a camera sensor system capable of capturing wavelengths of light in a visible spectrum;
the camera sensor system further capable of separately capturing wavelengths of light in the ultraviolet spectrum at approximately the same time the camera sensor system is capturing wavelengths of light in the visible spectrum;
a computer system coupled to the camera sensor system and configured to process the captured wavelengths of light in the visible spectrum to render a first digital image of the wavelengths of light in the visible spectrum;
the computer system further configured to process the captured wavelengths of light in the ultraviolet spectrum to render a second digital image of the wavelengths of light in the ultraviolet spectrum;
the computer system further configured to modify the second digital image to create a third digital image that is visible;
the computer system further configured to render a display image that is a composite of the first digital image of wavelengths of light in the visible spectrum and the third digital image of the modified second digital image; and
wherein the camera sensor system is further capable of separately capturing ultraviolet A wavelengths and ultraviolet B wavelengths,
the computer system is further configured to separately identify whether the identified one or more areas of interest lacks ultraviolet A protection and ultraviolet B protection; and
the computer system is further configured, when rendering the display image, to assign different false colors to the identified one or more areas of interest that lack ultraviolet A protection and the identified one or more areas of interest that lack ultraviolet B protection.

9. The mobile device of claim 8, wherein the computer system is configured to render the display image at approximately the same time the camera sensor captures the wavelengths of light in the visible spectrum.

10. The mobile device of claim 8, wherein: the camera sensor system comprises a first sensor assembly for capturing wavelengths of light in a visible spectrum and a second sensor assembly for capturing wavelengths of light in the ultraviolet spectrum.

11. The mobile device of claim 8, further comprising UV LEDs capable of turning on while the computer system is capturing wavelengths of light in the ultraviolet spectrum.

12. The mobile device of claim 8, wherein the third digital image is a black-and-white image.

13. The mobile device of claim 8, further comprising means to obtain information comprising a type of sunscreen; and wherein the display is further operable to display the type of sunscreen.

14. The mobile device of claim 8, further comprising means to obtain ultraviolet environment information; and wherein the display is further operable to display the environment information.

15. The mobile device of claim 8, wherein the display image shows the first digital image and the third digital image side by side.

16. A mobile device comprising:
a camera sensor system comprising a lens with an optical filter to filter out visible light;
the camera sensor system further capable of capturing wavelengths of light in the ultraviolet spectrum to create a first image;
a computer system configured to process the captured wavelengths of light in the ultraviolet spectrum to render a first digital image of the wavelengths of light in the ultraviolet spectrum;
the computer system further configured to modify the first digital image to create a display image that is visible;
the computer system further configured to render a display image on a display; and
wherein the computer system is configured to render the display image at approximately the same time the camera sensor captures the wavelengths of light in the ultraviolet spectrum; and
wherein the camera sensor system is further capable of separately capturing ultraviolet A wavelengths and ultraviolet B wavelengths, the computer system is further configured to separately identify whether the identified one or more areas of interest lacks ultraviolet A protection and ultraviolet B protection; and the computer system is further configured, when rendering the display image, to assign different false colors to the identified one or more areas of interest that lack ultraviolet A protection and the identified one or more areas of interest that lack ultraviolet B protection.

17. The mobile device of claim 16, wherein the display image is a black-and-white image.

18. The mobile device of claim 17, wherein the computer system is further configured to render the display image to show areas with sunscreen in a dark false color.

19. The mobile device of claim 17, wherein the display image is stored.

* * * * *